United States Patent
Slavazza et al.

(10) Patent No.: US 6,320,025 B1
(45) Date of Patent: Nov. 20, 2001

(54) SOLID PHASE PEPTIDE SYNTHESIS REACTION VESSEL

(76) Inventors: Dario Slavazza; Heng Wei Chang, both of 1300 Industrial Rd., San Carlos, CA (US) 94070

( * ) Notice: Subject to any disclaimer, the term of this patent is extended or adjusted under 35 U.S.C. 154(b) by 0 days.

(21) Appl. No.: 09/354,760

(22) Filed: Jul. 29, 1999

(51) Int. Cl.[7] ............................... A61K 38/00; B01J 8/00
(52) U.S. Cl. ........................ 530/334; 422/130; 422/131
(58) Field of Search ................................ 422/131, 134, 422/110, 111, 130, 101, 62; 210/321.88, 321.79, 321.87; 530/333, 334, 344

(56) References Cited

U.S. PATENT DOCUMENTS

| | | | |
|---|---|---|---|
| 4,192,798 | * 3/1980 | Verlander et al. | 530/334 |
| 4,242,461 | * 12/1980 | Bartoli et al. | 422/218 |
| 4,283,289 | * 8/1981 | Meyst et al. | 210/448 |

* cited by examiner

Primary Examiner—Hien Tran
(74) Attorney, Agent, or Firm—Richard Aron Osman

(57) ABSTRACT

Reaction vessels suitable for solid phase polymer synthesis generally comprise: a housing defining a chamber for containing a resin, said housing having an operable inlet port and an operable outlet port in fluid communication with said chamber; and an elongate resin filter having an interior bore, and adapted to enable filtered fluid flow from an exterior inlet surface thereof into the filter interior bore, said filter being disposed in said chamber and having an outlet connection fluidly coupling said filter interior bore to the housing outlet port such that fluid flowing through the housing inlet port into the chamber passes through the filter inlet surface, into the filter interior bore and out the housing outlet port.

11 Claims, 4 Drawing Sheets

SOLID PHASE PEPTIDE SYNTHESIS REACTION VESSEL

FIELD OF THE INVENTION

The field of the invention is a solid phase peptide synthesis reaction vessel.

BACKGROUND OF THE INVENTION

Large scale solid phase peptide synthesis requires consideration of a number of reactor design issues. The resin used is usually a gel resin with a low degree of cross-linking which swells in certain solvents (such as DCM), and shrinks in others (such as methanol). The resin volume tends also to increase with the growth of the peptide chain length. In addition, the resins tend to be fairly soft, and sensitive to physical attrition. Furthermore, the amount of exposure time between the peptide-resin and the solvents and reactants used in the synthesis is often critical. Deprotection of the resin-bound peptide must be complete in order to obtain the highest yield, but the resulting carbocations must not remain in contact with the peptide because of undesirable side-reactions that may occur. Unfortunately, the time required to drain the solution from a resin slurry suspension increases with the depth of the resin bed formed during filtration. Consequently, exposure time of resin-bound peptide to carbocations increases as bed depth increases. As a result, the filtration times for kilogram-scale reactions are far longer than those encountered in bench-scale reactions, so the risk of damage to the peptides due to reactions with carbocations increases with batch size. Larger scale reactors must therefore be designed in such a way as to minimize the filtration time.

Several attempts have been made to overcome the constraints imposed by the resins with tube reactor designs: Verlunder, et al., U.S. Pat. No. 4,192,798 (an industrial-scale HPLC type of reactor); Baru, et al., WO88/909010.6, SU 4117080 (a zero dead volume reactor in which one end of the reactor was allowed to float with the resin); Atherton, et al., JCS Chemical Communications, p. 1151 [1981] (a rigid polymer with macropores); Lapluye and Poisson WO 92/115867 (piston-type reactor with fritted ends); Birr, German Patent No. 2,017,351 and Stepaniuk et al. WO98/34633 ("washing machine" type reactors); and Anderson and Anderson, U.S. Pat. No. 5,186,824 (a centrifugal flooded "hollow rotor" reactor).

SUMMARY OF THE INVENTION

The invention provides methods and device for containing, reacting and filtering solid phase polymer synthesis resins. We disclose reaction vessel filtration systems that avoid both long and variable drain times and exorbitant costs often associated with scaling up solid phase peptide synthesis. The two main limitations to the speed of liquid removal in solid phase polymer syntheses are the surface area of the filters and the bed height of the resin (resin bed height or RBH). By using a tubular filtration system the filter surface area can be increased up to 10 fold over a flat filter and the RBH will not change significantly throughout the peptide synthesis. Thus extremely fast and uniform filtration can be achieved at a relatively low reaction vessel cost.

The subject reaction vessels generally comprise: a housing defining a chamber for containing a resin, said housing having an operable inlet port and an operable outlet port in fluid communication with said chamber; and an elongate resin filter having an interior bore, and adapted to enable filtered fluid flow from an exterior inlet surface thereof into the filter interior bore, said filter being disposed in said chamber and having an outlet connection fluidly coupling said filter interior bore to the housing outlet port such that fluid flowing through the housing inlet port into the chamber passes through the filter inlet surface, into the filter interior bore and out the housing outlet port; wherein said reaction vessel is suitable for solid phase polymer synthesis.

In more particular embodiments, the filter is cylindrical in shape; the vessel further comprises a hollow core filter holder within the housing and the filter is sheathed over the filter holder, wherein the filter comprises a closed end opposite the outlet connection, said closed end may be closed by a cap, and/or said holder secured to the housing by a threaded connection; the vessel further comprises means for functionally securing one or more of said filters to said housing; the chamber contains a solid phase polymer synthesis resin, which may comprise one or more bound amino acids, etc.

The invention provides methods of using the subject reaction vessels in polymer syntheses generally comprising constructing polymers in such vessels and isolating resultant polymers.

DESCRIPTION OF PARTICULAR EMBODIMENTS OF THE INVENTION

The following detailed description is offered by way of illustration and not by way of limitation:

The subject methods and devices are broadly applicable to a wide variety of liquid-solid reactions involving stepwise synthesis on solid substrates, such as the production of other polymers such as polynucleotides, polysaccharides, etc.

The subject reaction vessels generally comprise: a housing defining a chamber for containing a resin, said housing having an operable inlet port and an operable outlet port in fluid communication with said chamber; and an elongate resin filter having an interior bore, and adapted to enable filtered fluid flow from an exterior inlet surface thereof into the filter interior bore, said filter being disposed in said chamber and having an outlet connection fluidly coupling said filter interior bore to the housing outlet port such that fluid flowing through the housing inlet port into the chamber passes through the filter inlet surface, into the filter interior bore and out the housing outlet port; wherein said reaction vessel is suitable for solid phase polymer synthesis.

The elongate filter may be of a wide variety of shapes and porous materials suitable for large-scale polymer synthesis, and selected by cost, durability, sensitivity, etc.: (e.g. polyethylene, Teflon, polypropylene, etc.). Preferred materials are plastics, such as high density polyethylene (HDPE) having a defined pore size, such as 60 micron pore size. Such filters are commercially available, e.g. Porex Technologies (Fairbum Ga.). In particular embodiments, the filter is tubular, preferably cylindrical in shape, and/or extends at least 25%, preferably at least 50%, more preferably at least 75% of the chamber length between the housing inlet and outlet ports. In particular embodiments, the filters are from 1 to 30, preferably from 2 to 15, more preferably from 3 to 10 cm in cross section; from 10 to 100, preferably from 20 to 50 cm in length; and have a bore from 1 to 90% of the filter's cross section and from 50 to 100% of the filter's length. In general, the filter should be under the level of the liquid (solvent) so the solid support (resin) will cover the filters and become a filter itself, allowing the complete draining of the vessel.

Figure 1:
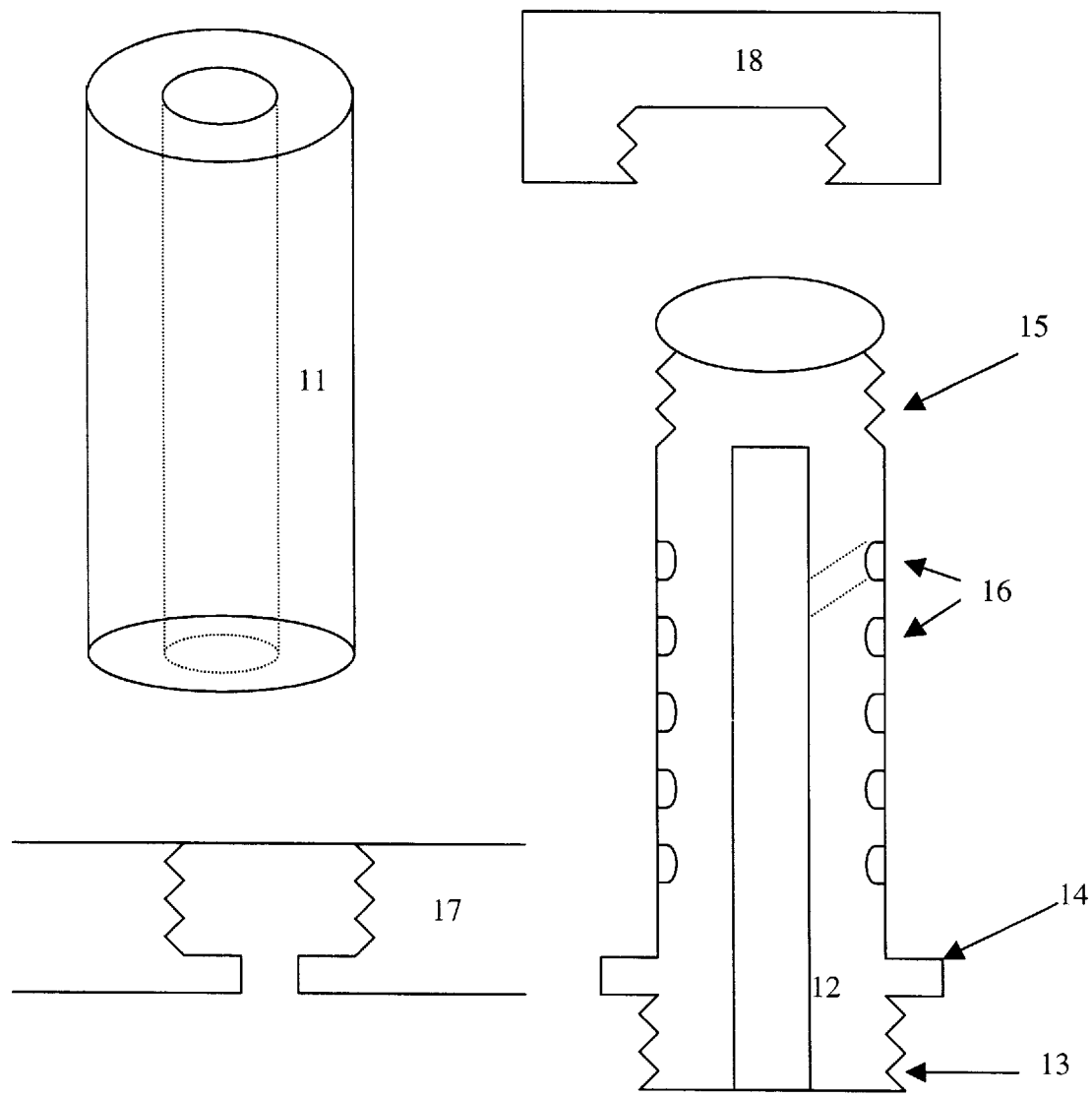
FIG. 1. Components of exemplary filtration system.
Figure 2:
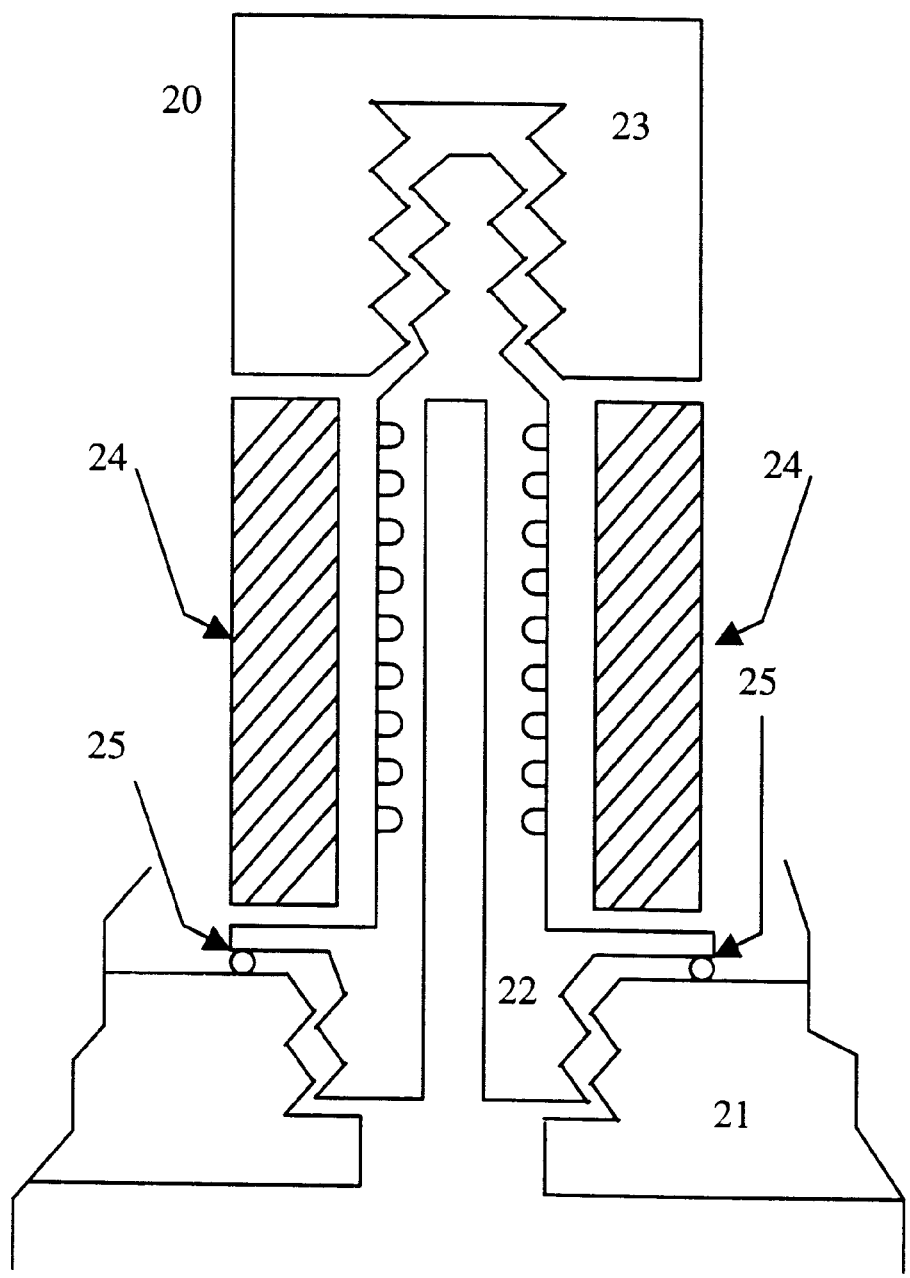
FIG. 2. Complete filter unit in cross-section.

In a particular embodiment, the filters are of HDPE material, having a bore the full length of the filter. In this embodiment, the filter end distal from the outlet port is sealed, for example with a screw-on cap. Alternatively, the filter may be secured, sheath-like over a holder, wherein the filter end distal from the outlet port is sealed by a compression fitting or cap applied to the holder, e.g. See FIG. 1. FIG. 1 shows the components of an exemplary filtration system employing a tubular filter 11. The system further includes a hollow core holder for the tubular filter 12 with threads at the base 13 for threading into the base of the reaction vessel 17 and a base 14 for the filter to seat onto and threads at the top 15 for the cap 18 to thread onto for holding the filter in place and holes 16 to allow the liquid into the hollow core and ultimately out of the reaction vessel. FIG. 2 is an example of a complete filter unit 20 screwed into a reaction vessel base 21 and comprised of a hollow core filter holder 22 and a holder cap 23 and a tubular filter 24 and an O-ring 25.

Figure 3:
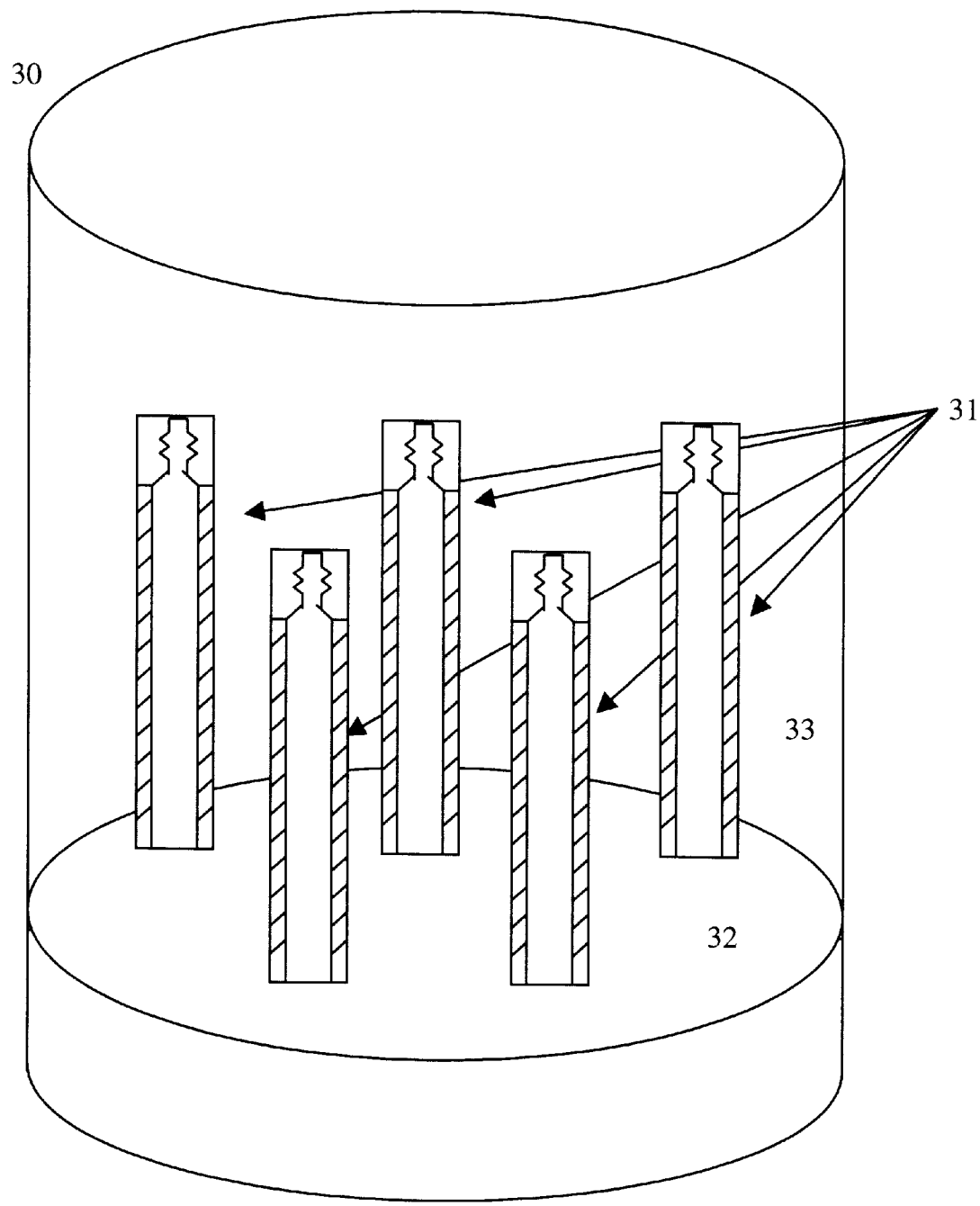
FIG. 3. Assembled reactor with five complete filter units.

The reaction vessel housing may be of any convenient shape and materials compatible with the targeted polymer synthesis and the required filter and ports. In a particular embodiment, the housing is a sealed glass cylinder adapted to accommodate a plurality, preferably at least 3, more preferably at least 5 filter assemblies. For example, FIG. 3 shows an exemplary solid phase reactor 30 with five complete filter units 31, a base 32 and a tubular glass walled vessel 33.

The vessel provides operable (open and closeable) chamber inlet and outlet ports, which may be of any convenient design compatible with the subject methods and devices. For example, inlet and outlet ports may be opened and closed with commercially available Teflon diaphragm valves (Furon, Anaheim Calif.).

Figure 4:
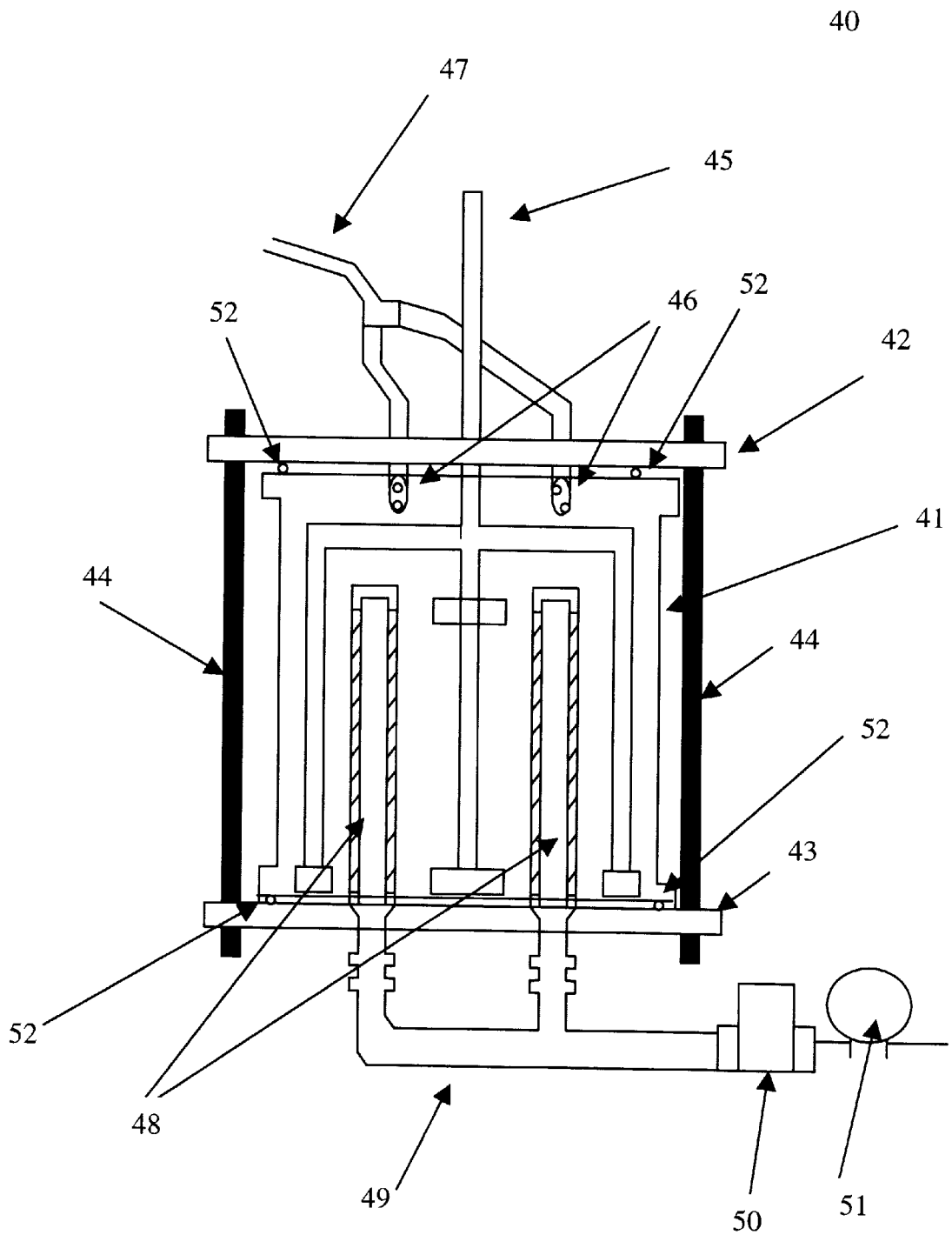
FIG. 4. Complete reaction vessel with tubular filtration system.

The vessel may also be adapted to provide resin mixing during one or more synthetic reaction steps. A wide variety of means for mixing may be applied, including a mechanical paddle, stir bar or other like device within the chamber, a bubble generator, a vessel rocking, shaking or swirling device, etc. For example, FIG. 4 shows an exemplary complete reaction vessel with the tubular filtration system 40, comprising a glass cylindrical vessel body 41 with a stainless steel top 42 and a stainless steel bottom 43 held together with stainless steel tie rods 44 and sealed with Teflon gaskets 52. Also shown is a stirring apparatus 45, filters 48, and shower balls 46 connected to the solvent input line 47. At the bottom is the solvent removal line 49 with a 2-way valve 50 and a solvent pump 51.

The vessel may be adapted to accommodate a wide variety of resins and reaction chemistries. In a particular embodiment, the vessel contains a solid phase polymer resin, preferably a solid phase peptide synthesis resin, such as crossed linked polystyrene, e.g. 1, 2, etc. %, crossed linked polystyrene. In more particular embodiments, the vessel is adapted to large scale synthesis, and/or contains at least 10, preferably at least 100, more preferably at least 1,000, more preferably at least 10,000 g resin (dry weight). Such embodiments are capable of simultaneously activating and coupling 100 g amino acid per step and provide yields of from 100 to 5,000 g decapeptides. Solid phase polymer synthesis reaction chemistries are widely known in the art. For example, a typical peptide synthesis is conducted by the following procedure: The N-terminus of the resin-bound peptide (protected by boc) is deblocked in a solution of trifluoroacetic acid (TFA) in dichloromethane (DCM), for example. The next amino acid in the sequence is coupled to the resin-bound peptide with coupling agent such as dicyclohexyclcarbodiimide (DCC) in a solution of DCM and dimethyl formamide (DMF), for example. An activating agent such as 1-hydroxybenzotrazole (HOBt) may be used to improve rate and selectivity of the coupling reaction and to decrease racemization. The unreacted amino acid, reagents, and by-products are removed from the resin by washing and filtration. The washing and filtration process is then repeated. The N-terminus of the peptide is then deblocked; another peptide is added to the chain, the system is then washed and filtered, etc. The process is repeated until all the desired amino acids have been added to the peptide chain in the desired order. The remaining blocking groups are then removed from the peptide, the peptide is cleaved from the resin, and the peptide is collected.

All publications and patent applications cited in this specification and all references cited therein are herein incorporated by reference as if each individual publication or patent application or reference were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A solid phase polymer synthesis reaction vessel comprising:

a housing defining a chamber containing a solid phase polymer synthesis resin, said housing having an operable inlet port and an operable outlet port in fluid communication with said chamber; and an elongate resin filter having an interior bore, and adapted to enable filtered fluid flow from an exterior inlet surface thereof into the filter interior bore, said filter being disposed in said chamber and having an outlet connection fluidly coupling said filter interior bore to the housing outlet port such that fluid flowing through the housing inlet port into the chamber containing said resin passes through the filter exterior inlet surface, into the filter interior bore and out the housing outlet port;

said reaction vessel suitable for solid phase polymer synthesis.

2. A vessel according to claim 1 wherein the filter is cylindrical in shape.

3. A vessel according to claim 1 wherein the vessel further comprises a hollow core filter holder within the housing and the filter is sheathed over the filter holder.

4. A vessel according to claim 1 wherein the vessel further comprises a hollow core porous filter holder within the housing and the filter is sheathed over the filter holder, the filter comprises a closed end opposite the outlet connection and said closed end is closed by a cap.

5. A vessel according to claim 1 wherein the vessel further comprises a hollow core porous filter holder within the housing and the filter is sheathed over the filter holder, the filter comprises a closed end opposite the outlet connection, said closed end is closed by a cap and said holder is secured to the housing by a threaded connection.

6. A vessel according to claim 1 wherein the vessel further comprises means for functionally securing said filter to said housing.

7. A vessel according to claim 1 comprising more than one said filter.

8. A vessel according to claim 1 wherein said resin is a solid phase peptide synthesis resin comprising one or more bound amino acids.

9. A method of solid phase polymer synthesis comprising the steps of constructing a polymer in a vessel according to claim 1 and isolating the polymer.

10. A solid phase polymer synthesis reaction vessel comprising:

- a housing defining a chamber containing a solid phase polymer synthesis resin, said housing having an inlet and an outlet; and
- a tubular resin filter within the housing and defining a bore with a closed end and an open end, said open end surrounding said outlet so that a fluid flowpath may be formed from said inlet, into said chamber containg said resin, through said filter, into said bore, and out said open end and said outlet; wherein,
- said resin is a solid phase peptide synthesis resin comprising one or more bound amino acids;
- the filter is cylindrical in shape;
- the vessel further comprises a hollow core porous filter holder within the housing and the filter is sheathed over the filter holder, said closed end is closed by a cap and said holder is secured to the housing by a threaded connection; and
- the vessel comprises more than one said filter.

11. A method of solid phase peptide synthesis comprising the steps of constructing a peptide in a vessel according to claim 10 and isolating the peptide.

* * * * *